(12) United States Patent
Samec et al.

(10) Patent No.: US 11,002,132 B2
(45) Date of Patent: May 11, 2021

(54) SAMPLING CHAMBER WITH HYDROGEN SULFIDE-REACTIVE SCAVENGER

(71) Applicant: Halliburton Energy Services, Inc., Houston, TX (US)

(72) Inventors: William Wade Samec, Katy, TX (US); Cato Russell McDaniel, Montgomery, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/529,216

(22) Filed: Aug. 1, 2019

(65) Prior Publication Data

US 2019/0390548 A1  Dec. 26, 2019

Related U.S. Application Data

(62) Division of application No. 14/916,293, filed as application No. PCT/US2013/063299 on Oct. 3, 2013, now Pat. No. 10,415,381.

(51) Int. Cl.
*E21B 49/08* (2006.01)
*G01N 33/28* (2006.01)
*E21B 49/10* (2006.01)

(52) U.S. Cl.
CPC .......... *E21B 49/081* (2013.01); *E21B 49/086* (2013.01); *E21B 49/088* (2013.01); *E21B 49/10* (2013.01); *G01N 33/287* (2013.01); *E21B 49/0875* (2020.05)

(58) Field of Classification Search
None
See application file for complete search history.

(56) References Cited

U.S. PATENT DOCUMENTS

| 6,223,822 B1* | 5/2001 | Jones | E21B 49/10 166/250.05 |
| 2008/0066904 A1* | 3/2008 | Van Hal | E21B 49/10 166/250.1 |

OTHER PUBLICATIONS

Aften et al. "New Compounds for Hydrogen Sulfide Scavenging and Iron Sulfide Control", SPE 141286, 2011 (Year: 2011).*

* cited by examiner

*Primary Examiner* — Charles R Nold
(74) *Attorney, Agent, or Firm* — Chamberlain Hrdlicka

(57) ABSTRACT

Systems, methods and devices for analyzing a sample of fluid extracted from a hydrocarbon-producing geological formation to detect a quantitative amount of hydrogen sulfide or disclosed. The systems methods and devices involve including a scavenger within a sample compartment to react with the hydrogen sulfide therein. The concentration of hydrogen sulfide in the sample may be derived as a function of the amount of scavenger remaining in the sample after reaction with hydrogen sulfide, an amount of byproduct of a reaction between the scavenger and the hydrogen sulfide, or an amount of hydrogen sulfide as measured following a secondary reaction that releases the hydrogen sulfide from the scavenger.

16 Claims, 6 Drawing Sheets

SAMPLING CHAMBER WITH HYDROGEN SULFIDE-REACTIVE SCAVENGER

FIELD OF THE INVENTION

The present disclosure relates generally to the recovery of subterranean deposits and more specifically to methods and systems for analyzing fluid within a wellbore to determine the concentration of hydrogen sulfide gas present within a fluid sample taken from the wellbore.

DESCRIPTION OF RELATED ART

Wells are drilled at various depths to access and produce oil, gas, minerals, and other naturally-occurring deposits from subterranean geological formations. The drilling of a well is typically accomplished with a drill bit that is rotated within the well to advance the well by removing topsoil, sand, clay, limestone, calcites, dolomites, or other materials. The drill bit is typically attached to a drill string that may be rotated to drive the drill bit and within which drilling fluid, referred to as "drilling mud" or "mud", may be delivered downhole. The drilling mud is used to cool and lubricate the drill bit and downhole equipment and is also used to transport any rock fragments or other cuttings to the surface of the well.

As wells are established it is often useful to obtain information about the well and the geological formations through which the well passes and fluid in the wellbore, including the fluid to be extracted from the formations. Information gathering is typically performed using tools that are delivered downhole by wireline or alternatively tools that are coupled to or integrated into the drill string. Wireline-delivered tools are suspended from a wireline that is electrically connected to control and logging equipment at the surface of the well. The tools may be deployed by first removing the drill string and then lowering the wireline and tools to an area of interest within the formation. This type of testing and measurement is often referred to as wireline formation testing ("WFT"). The tools associated with WFT may be used to measure pressure, temperature, and other properties of formation and wellbore fluids.

Instead of wireline deployment, measurement tools are sometimes coupled to or integrated with the drill string. In these situations, the added expense and time of removing the drill string prior to measurement of important formation properties is avoided. This process of measurement while drilling ("MWD") uses measurement tools to determine formation and wellbore temperatures and pressures, as well as the trajectory of the drill bit. A similar process, logging while drilling ("LWD"), uses tools to determine additional formation properties such as permeability, porosity, resistivity, and other properties. In some cases, the information obtained by MWD and LWD allow operators to make real-time decisions and changes to ongoing drilling operations.

In MWD and LWD applications, it is often desired to collect a representative sample of formation or reservoir fluids (typically hydrocarbons) to further evaluate drilling operations and production potential, or to detect the presence of certain gases or other materials in the formation that may affect well performance. For example, hydrogen sulfide (H2S), a poisonous, corrosive, and flammable gas can occur in formation fluids, and its presence in the wellbore in significant concentrations may result in damage to wellbore, components or dangerous conditions for well operators at the surface.

DETAILED DESCRIPTION OF ILLUSTRATIVE EMBODIMENTS

Figure 1A:
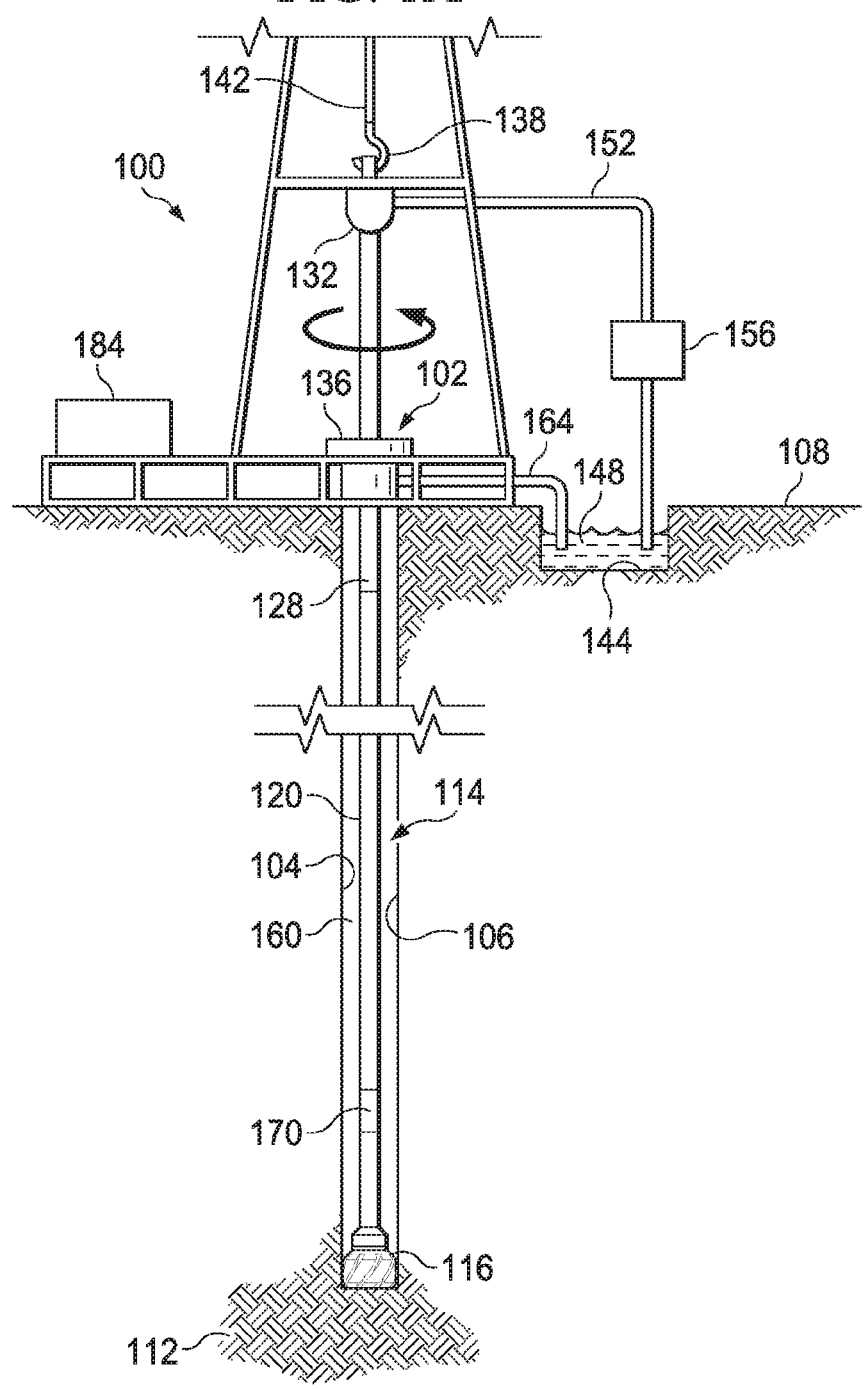
FIG. 1A illustrates a schematic view of a well in which an illustrative embodiment of a fluid sampling system is deployed in an LWD assembly.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The systems and methods described herein provide for the sampling of formation fluid being extracted from wells either during or after drilling operations to determine the extent to which hydrogen sulfide gas (H2S) is present within the fluid. H2S is a volatile chemical compound that oxidizes easily, is corrosive to downhole tools, and is poisonous and explosive. The presence of H2S in a formation may increase the cost of harvesting and processing fluid from the formation and present a safety hazard to well operators.

In small quantities, H2S may also be difficult to detect. H2S reacts with many surfaces and other elements in the wellbore as it travels with the formation fluid to the surface. Since a quantity of H2S will have reacted out of the fluid before it reaches the surface, the H2S may not be detectable by a system that gathers samples from fluid extracted from a well as the fluid reaches the surface. Such reactions may damage wellbore components, corrode surfaces, and render small amounts of H2S undetectable. Another disadvantage of systems that detect H2S at the surface is that a well operator who has detected H2S will still not know with any specificity the location from which the H2S originated within the formation and will be ignorant of H2S concentration gradients that may exist in the formation.

The systems and methods described herein provide for the determination of a quantitative concentration of H2S at specific locations in a formation by using a fluid sampling tool that is capable of taking fluid samples from various depths and locations within the formation and logging location data that indicates the location in the formation from which the sample was taken. The fluid sampling tool may include an additive or scavenger within a sampling chamber of the fluid sampling tool. As referenced herein, a "scavenger" is generally understood to be a chemical substance added to a mixture to remove or deactivate impurities or unwanted reaction products in the mixture, and a "scavenger volume" is a mass or volume of a scavenger material. It is noted that while H2S is referenced as the subject impurity, other contaminants may be tested for and measured using the disclosed systems and methods.

With respect to H2S, for example, a scavenger may exhibit a rapid, quantitative reaction with the sulfide that eliminates the presence of free H2S in the fluid or selectively absorbs the H2S. The scavenger may be inserted into the sampling chamber prior to deployment in the wellbore, and may be composed of (for example) metals such as iron, zinc, copper, or silver; metal salts such as ferrous gluconate, zinc salts, or silver salts; organic scavengers such as reactive aldehyde (including formaldehyde, acrolein, and glyoxal) and amines. The scavenger may be deployed as a solid mass, as a suspended particulate in a fluid, such as distilled water, or in any other suitable manner.

The fluid sampling tool may be used to gather a fluid sample from the wellbore for analysis, and the fluid sample may be analyzed to determine the concentration of H2S within the formation fluid. Illustrative methods of determining the concentration of H2S include measuring the concentration of a byproduct created when the scavenger reacts with H2S; measuring the concentration of any leftover scavenger that did not react with H2S; and causing an additional reaction within the fluid sample to extract the H2S from the byproduct created from the scavenger reacting with the H2S, and then directly measuring the concentration of H2S.

The fluid sampling tools described herein may vary in design but typically include an inlet, an outlet, at least one fluid sampling chamber that includes one or more sampling compartments, and a scavenger or scavenger volume, within the compartment(s). The inlet and outlet may be fluidly connected to fluid within a wellbore that is being extracted from a geological formation. The illustrative embodiments described below relate to the analysis of such fluid for the purpose of determining the quantitative amount of H2S (or other contaminant) present within the fluid.

The fluid sampling tools, systems and methods described herein may be used with any of the various techniques employed for evaluating a well, including without limitation wireline formation testing (WFT), measurement while drilling (MWD), and logging while drilling (LWD). The various tools and sampling units described herein may be delivered downhole as part of a wireline-delivered downhole assembly or as a part of a drill string. It should also be apparent that given the benefit of this disclosure, the apparatuses and methods described herein have applications in downhole operations other than drilling, and may also be used after a well is completed.

As used herein, the phrases "fluidly coupled," "fluidly connected," and "in fluid communication" refer to a form of coupling, connection, or communication related to fluids, and the corresponding flows or pressures associated with these fluids. Reference to a fluid coupling, connection, or communication between two components describes components that are associated in such a way that a fluid can flow between or among the components.

Figure 1B:
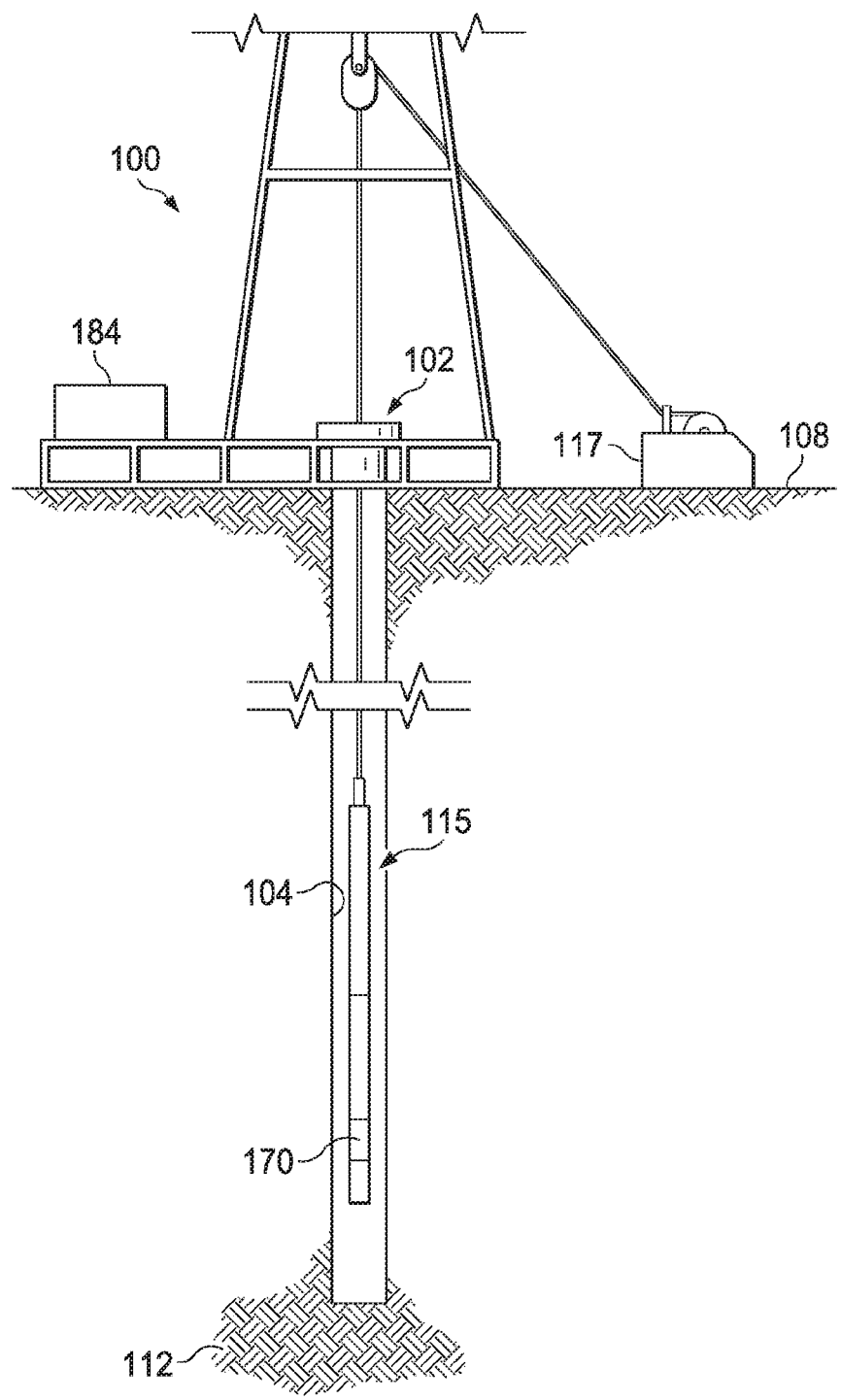
FIG. 1B illustrates a schematic view of a well in which the fluid sampling system of FIG. 1A is deployed in a wireline or WFT assembly.
Figure 1C:
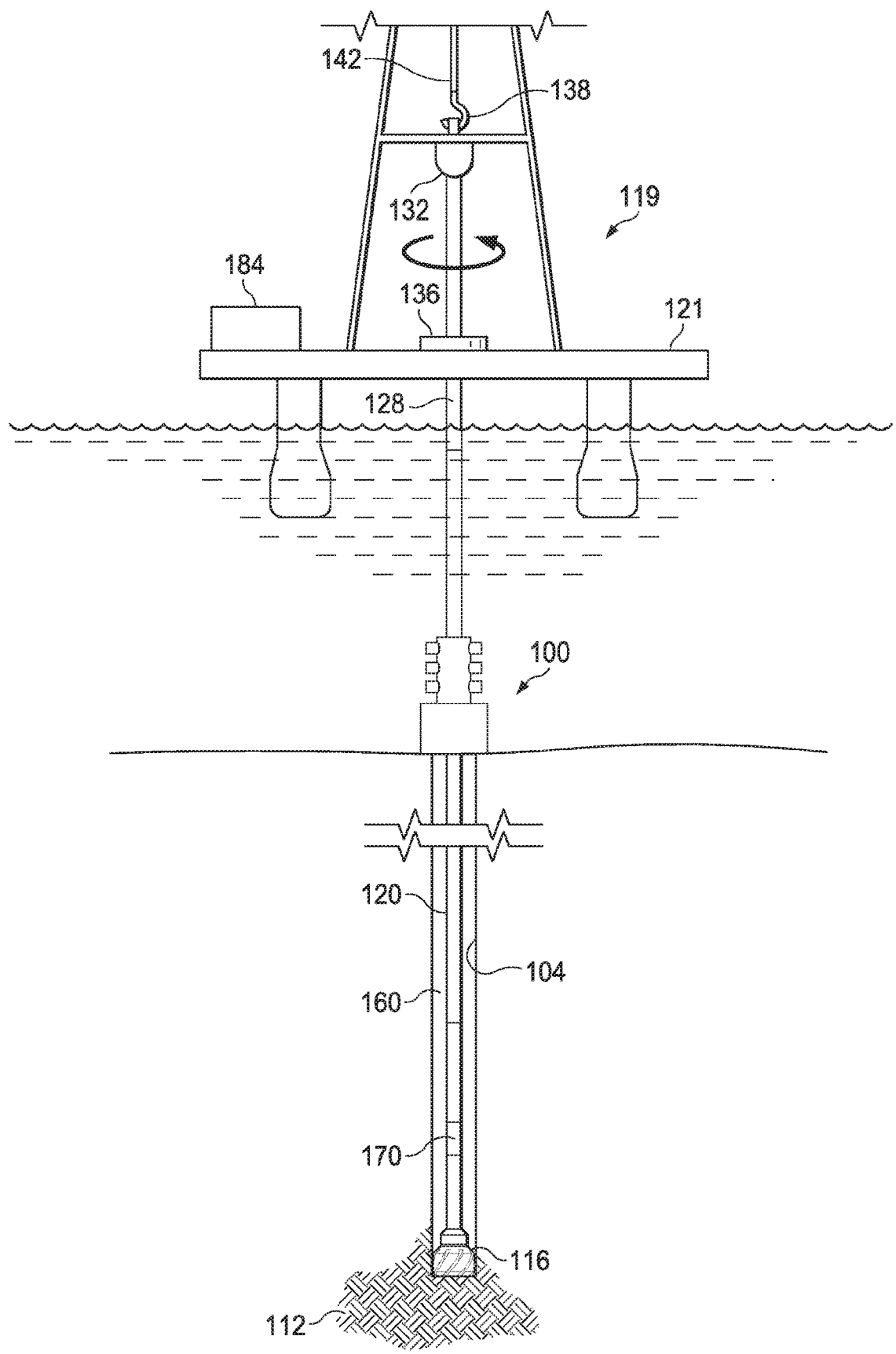
FIG. 1C illustrates a schematic view of a subsea well in which the fluid sampling system of FIG. 1A is deployed.

Referring now to FIGS. 1A-1C, a fluid sampling and analysis system 100 according to an illustrative embodiment is used in a well 102 having a wellbore 104 that extends from a surface 108 of the well to or through a subterranean geological formation 112. The well 102 is illustrated onshore in FIG. 1A with the fluid sampling and analysis system 100 being deployed in an LWD assembly 114. Alternatively, fluid sampling and analysis system 100 may instead be deployed as part of a wireline assembly 115 (see FIG. 1B), either onshore or off-shore. The wireline assembly 115 includes a winch 117 to lift and lower a downhole portion of the wireline assembly 115 into the well. In still another embodiment, the fluid sampling and analysis system 100 may be deployed in a sub-sea well 119 accessed by a fixed or floating platform 121. FIGS. 1A-1C each illustrate these possible uses of the fluid sampling and analysis system 100, and while the following description of the fluid sampling and analysis system 100 focuses primarily on the use of the fluid sampling and analysis system 100 with the LWD assembly 114 of FIG. 1A, the fluid sampling and analysis system 100 may be used instead in the well configurations illustrated in FIGS. 1B and 1C, as well as in other well configurations where it is desired to sample a fluid. Similar components in FIGS. 1A-1C are identified with similar reference numerals.

In the embodiment illustrated in FIG. 1A, the well 102 is formed by a drilling process in which a drill bit 116 is turned by a drill string 120 that extends from the drill bit 116 to the surface 108 of the well 102. The drill string 120 may be made up of one or more connected tubes or pipes, of varying or similar cross-section. The drill string may refer to the collection of pipes or tubes as a single component, or alternatively to the individual pipes or tubes that comprise the string. The term drill string is not meant to be limiting in nature and may refer to any component or components that are capable of transferring rotational energy from the surface of the well to the drill bit. In several embodiments, the drill string 120 may include a central passage disposed longitudinally in the drill string and capable of allowing fluid communication between the surface of the well and downhole locations.

At or near the surface 108 of the well, the drill string 120 may include or be coupled to a kelly 128. The kelly 128 may have a square, hexagonal or octagonal cross-section. The kelly 128 is connected at one end to the remainder of the drill string and at an opposite end to a rotary swivel 132. The kelly passes through a rotary table 136 that is capable of rotating the kelly and thus the remainder of the drill string 120 and drill bit 116. The rotary swivel 132 allows the kelly 128 to rotate without rotational motion being imparted to the rotary swivel 132. A hook 138, cable 142, traveling block (not shown), and hoist (not shown) are provided to lift or lower the drill bit 116, drill string 120, kelly 128 and rotary swivel 132. The kelly 128 and swivel 132 may be raised or lowered as needed to add additional sections of tubing to the drill string 120 as the drill bit 116 advances, or to remove sections of tubing from the drill string 120 if removal of the drill string 120 and drill bit 116 from the well 102 is desired.

A reservoir 144 is positioned at the surface 108 and holds drilling mud 148 for delivery to the well 102 during drilling operations. A supply line 152 is fluidly coupled between the reservoir 144 and the inner passage of the drill string 120. A pump 156 drives fluid through the supply line 152 and downhole to lubricate the drill bit 116 during drilling and to carry cuttings from the drilling process back to the surface 108. After traveling downhole, the drilling mud 148 returns to the surface 108 by way of an annulus 160 formed between the drill string 120 and the wellbore 104. At the surface 108, the drilling mud 148 is returned to the reservoir 144 through a return line 164. The drilling mud 148 may be filtered or otherwise processed prior to recirculation through the well 102.

A fluid sampling tool 170 may be positioned downhole to obtain fluid samples from the formation for analysis, and to measure, process, and communicate data regarding the formation, fluid from the formation, or other operations occurring downhole. This information, including information gathered from analysis of the fluid sample, allows well operators to determine, among other things, the concentration H2S within the fluid being extracted from the formation 112 to make intelligent decisions about ongoing operation of the well. In some embodiments, the data measured and collected by the fluid sampling tool 170 may include, without limitation, pressure, temperature, flow, acceleration (seismic and acoustic), and strain data. While the fluid sampling tool 170 is illustrated as a part of the drill string 120 in FIG. 11A, in other embodiments, the fluid sampling tool 170 may be lowered into the well by wireline (see FIG. 1B) either through the central passage of the drill string 120, or if the drill string 120 is not present, directly through the wellbore 104. As described in more detail below, the fluid sampling tool 170 may include a communications subsystem, including a transceiver for communicating using mud pulse telemetry or another suitable method of wired or wireless communication with a surface controller 184. The transceiver may transmit data gathered by the fluid sampling tool 170 or receive instructions from a well operator via the surface controller 184 to operate the fluid sampling tool 170.

Referring now to FIGS. 2-4B, a fluid sampling tool 170 is illustrated as a tool for gathering fluid samples from a formation for subsequent analysis and testing. In an embodiment, the fluid sampling tool 170 includes a transceiver 202 through which the fluid sampling tool 170 may communicate with other actuators and sensors in a drill string, the drill string's communications system, and with a surface controller. In an embodiment, the transceiver 202 is also the port through which various actuators (e.g. valves) and sensors (e.g., temperature and pressure sensors) in the fluid sampling tool 170 are controlled and monitored by, for example, a computer in another part of the drill string (not shown) or by the surface controller 184. In an embodiment, the transceiver 202 includes a computer that exercises the control and monitoring function.

The fluid sampling tool 170 may include a dual probe section 204, which extracts fluid from the formation 112, as described in more detail below, and delivers it to a channel 206 that extends from one end of the fluid sampling tool 170 to the other. The channel 206 can be connected to other tools or portions of the fluid sampling tool 170 arranged in series. The fluid sampling tool 170 may also include a gauge section 208, which includes sensors to allow measurement of properties, such as temperature and pressure, of the fluid in the channel 206. The fluid sampling tool 170 may also include a flow-control pump-out section 210, which includes a pump 212 for pumping fluid through the channel 206. The fluid sampling tool 170 also includes one or more chambers, such as multi-chamber sections 214, which are described in more detail below.

In an embodiment, the dual probe section 204 includes two probes 218, 220 which extend from the fluid sampling tool 170 and press against the borehole wall to receive fluid for sampling. Probe channels 222, 224 connect the probes 218, 220 to the channel 206. The pump 212 can be used to pump fluids from the reservoir, through the probe channels 222, 224 and to the channel 206. Alternatively, a low volume pump 226 can be used for this purpose. Two standoffs or stabilizers 228, 230 hold the fluid sampling tool 170 in place as the probes 218, 220 press against the borehole wall to receive fluid. In an embodiment, the probes 218, 220 and stabilizers 228, 230 are retracted when the tool is in motion and are extended to gather samples of fluid from the formation.

Figure 2:
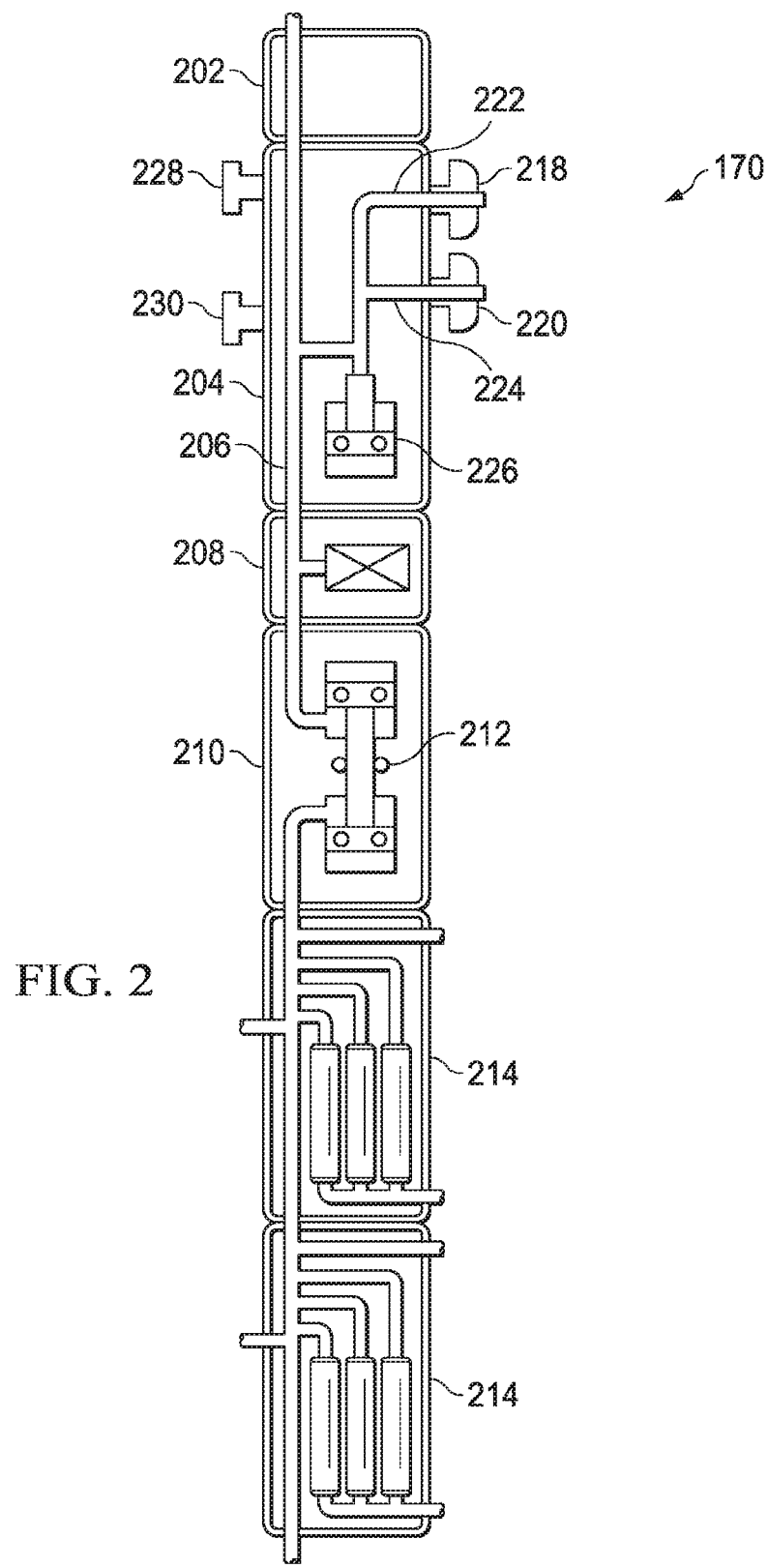
FIG. 2 depicts an enlarged schematic view of an illustrative embodiment of a fluid sampling tool for use in the fluid sampling system of FIG. 1A.
Figure 3:
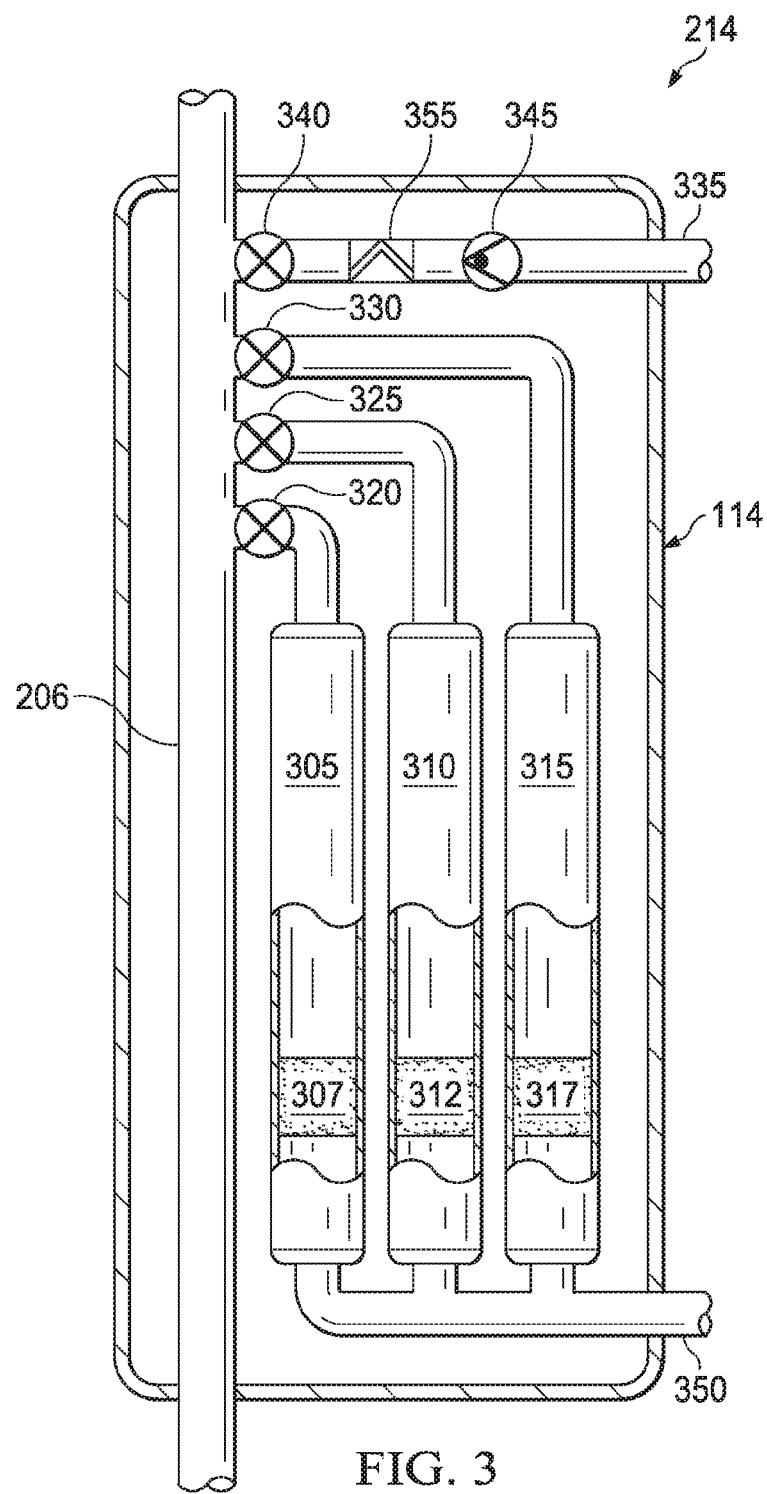
FIG. 3 depicts an enlarged schematic view of an illustrative embodiment of a fluid sampling chamber for use in the fluid sampling system of FIG. 1A.

In an embodiment, the multi-chamber sections 214 include multiple sample chambers 305, 310, 315, as shown in FIG. 3. While FIGS. 2 and 3 show the multi-chamber sections 214 having three sample chambers 305, 310, 315, it will be understood that the multi-chamber sections 214 can have any number of sample chambers and may in fact be single chamber sections.

In an embodiment, the sample chambers 305, 310, 315 are coupled to the channel 206 through respective chamber valves 320, 325, 330. Formation fluid can be directed from the channel 206 to a selected sample chamber by opening the appropriate chamber valve. For example, formation fluid can be directed from the channel 206 to sample chamber 305 by opening chamber valve 320, formation fluid can be directed from the channel 206 to sample chamber 310 by opening chamber valve 325, and formation fluid can be directed from the channel 206 to sample chamber 315 by opening chamber valve 330. The valves 320, 325, 330 may be configured such that when one chamber valve is open the others are closed.

In an embodiment, the multi-chamber sections 214 include a path 335 from the channel 206 to the annulus 160 through a valve 340. Valve 340 is open during the drawdown period when the formation tester is clearing mud cake, drilling mud, and other contaminants into the annulus before clean formation fluid is directed to one of the sample chambers 305, 310, 315. A check valve 345 prevents fluids from the annulus 160 from flowing back into the channel 206 through the path 335. As such, the multi-chamber sections 214 may include a path 350 from the sample chambers 305, 310, 315 to the annulus 160.

Figure 4A:
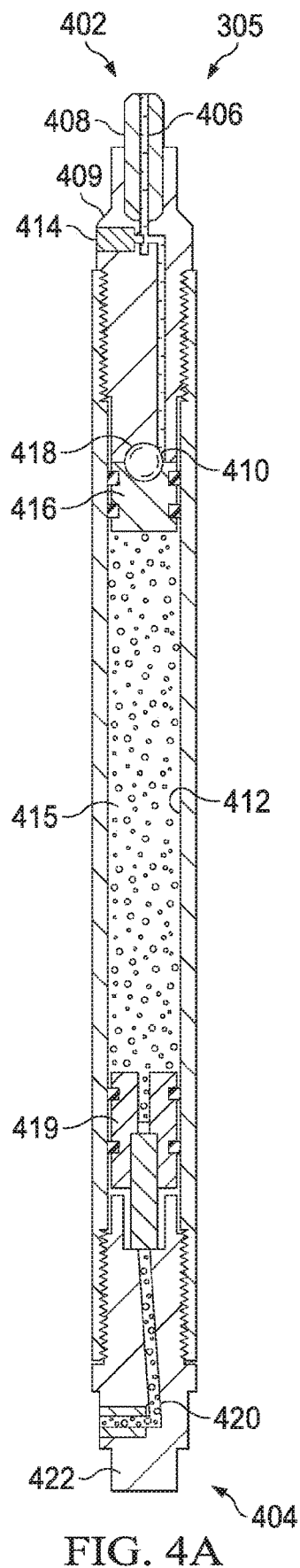
FIG. 4A depicts an enlarged schematic view of an illustrative embodiment of a fluid sampling compartment of the fluid sampling chamber of FIG. 3 prior to receiving fluid from the formation.

An illustrative embodiment of a sample chamber 305, 310, or 315 is shown in FIG. 4A, which show, respectively, a sample chamber before and after a sample is taken. In an embodiment, the sample chamber 305 has a channel end 402 and an annulus end 404. At the channel end 402, the sample chamber includes an inlet port 406 which communicates with the channel 206 through valve 320, as shown in FIG. 3. In an embodiment, the inlet port 406 proceeds through a connector 408 and a seal 409 to a vent 410 into a sample compartment 412. In an embodiment, the inlet port can be sealed by a valve 414, which provides a sufficient seal that allows the sample chamber 305 to be safely shipped to a lab for analysis after removal from the fluid sampling tool 170.

In an embodiment, as shown in FIG. 4A, the inlet port 406 is sealed by a sample piston 416, which is capable of traveling the entire length of the sample compartment 412. The sample piston 416 divides the sample compartment 412 into a sample side 413 on the side of the sample compartment 412 closest to the channel end 402 (shown most clearly in FIG. 4B), and a nitrogen side 415 on the side of the sample compartment 412 closest to the annulus end 404, as shown in FIG. 4A. The sizes of the sample side 413 and the nitrogen side 415 may vary with movement of the sample piston 416. In the illustrative embodiment of FIG. 4A, the nitrogen side 415 of the sample compartment 412 is pressurized, for example with nitrogen gas, which causes the sample piston 416 to move toward the channel end 402 and seal the inlet port 406. The pressurization of the nitrogen side 415 of the sample compartment 412 may take place at the surface before the sample chamber 305 is inserted into the fluid sampling tool 170.

In an embodiment, the end of the sample compartment 412 closest to the annulus end 404 of the sample chamber 305 is sealed by an annulus piston 419, which moves back and forth within the sample compartment 412. An annulus path 420 communicates annulus fluids through an annulus seal 422 to the annulus piston 419, which moves to compress the fluid in the sample compartment 412 until its pressure substantially matches the annulus pressure. In an embodiment in which the annulus piston 419 is not present, the sample piston 416 may perform the same function of compressing the fluid in the sample compartment 412 until its pressure is at equilibrium with the annulus pressure.

Figure 4B:
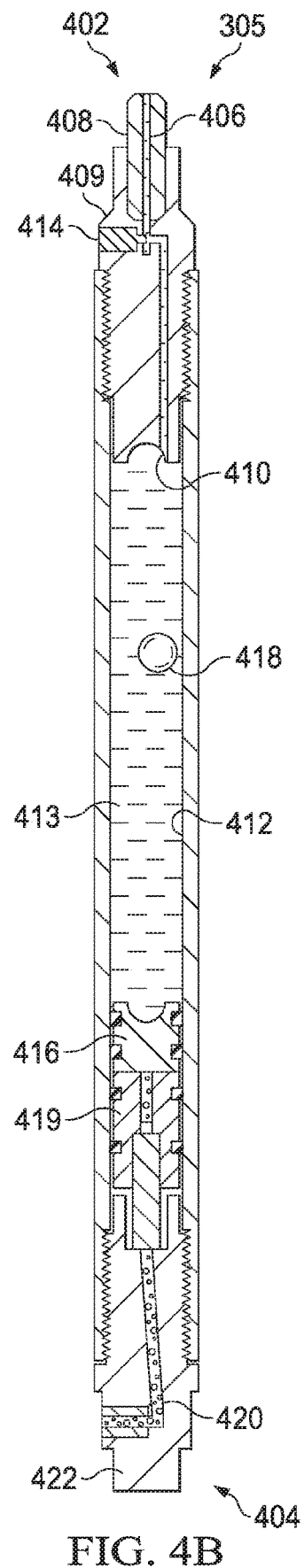
FIG. 4B depicts an enlarged schematic view of an illustrative embodiment of a fluid sampling compartment of the fluid sampling chamber of FIG. 3 after receiving fluid from the formation.

In the embodiment shown in FIG. 4B, a sample of formation fluid has been pumped into the sample side 413 of the sample compartment 412 by, for example, pressing or extending one or both of the probes 218, 220 shown in FIG. 2 against the borehole wall. During the extension of the probes 218, 220, one or both of the stabilizers 228, 230 may be extended to hold the fluid sampling tool 170 in place laterally within the borehole by pressing against the opposing side of the borehole wall. As the probes 218, 220 are pressed against the borehole wall, the valve 340 opening path 335 may be opened and the pump 212 engaged until a determination is made that uncontaminated fluid is being drawn through the probes 218, 220 from the formation. The valve 340 may then be closed and the valves 320 and 414 opened to allow the fluid to flow through the inlet port 406 and through the vent 410 to engage the sample piston 416. Pressure developed by the pump may be sufficient to overcome the annulus pressure, thereby causing the sample piston 416 to retract into the sample compartment 412 and the sample side 413 to allow the fluid to fill the sample compartment 412. The sample side 413 of the sample compartment 412 may be filled until it reaches the state shown in FIG. 4B, wherein the sample piston 416 is at rest against the annulus piston 419. Valve 320 may then be closed to seal the inlet port 406 and the sample compartment 412.

As shown in the embodiments of FIGS. 4A and 4B, the sample chamber 305 includes a scavenger volume 418 that is free to interact with the fluid in the sample side 413 of the sample chamber 305. In an embodiment, the scavenger volume 418 is a sphere or similar-shaped object that comprises a volume of a substance that is selected to remove or deactivate impurities or unwanted reaction products in a fluid. In another embodiment, the scavenger volume is a liquid. Where the impurity is H2S, the scavenger is a material that is capable of a rapid, quantitative reaction with the H2S. In an embodiment, the scavenger volume 418 is sized to include a sufficient amount of scavenger material to react with a maximum estimated amount of H2S that may enter the sample compartment 412 in order to react with the entire amount of free H2S in the fluid sample.

The scavenger volume may be in the font of a sphere, as shown in FIGS. 4A and 4B, one or more smaller spheres, a solid mass having any other suitable shape, such as a cube, cylinder, or other prism. In another embodiment, the scavenger volume 418 may be pellets, a powder, a liquid, or a gas that is released into the fluid after the sample compartment 412 has been sealed.

The scavenger volume 418 may also be free to move within the sample compartment 412 when the sample side 413 of the sample compartment 412 is partially or completely filled with fluid. In an embodiment, the sample piston 416 releases the scavenger volume 418 so that it can move within the sample compartment 412 as the sample compartment 412 fills. In an embodiment, the scavenger volume 418 is tethered by a flexible or rigid member within the sample compartment 412.

In an embodiment, a sample chamber 305 is prepared for deployment into a well by inserting a scavenger volume 418 into the sample side 413 of the sample compartment 412, and pressurizing the nitrogen side 415 of the sample compartment 412 with, for example, nitrogen. The prepared sample chamber 305 is then placed in the fluid sampling tool 170, which is in turn lowered into position in the wellbore, as shown in FIGS. 1A-1C.

In the operation of an illustrative embodiment, fluid from the formation is pumped into the sample side 413 of the sample chamber 305. The sample chamber 305 is then sealed by, for example, closing valve 320, as shown in FIG. 3. After the sample chamber is filled, the scavenger volume 418 is in contact with the fluid from the formation. If H2S is present within the fluid, the scavenger volume 418 will begin reacting with the H2S once the fluid and scavenger volume 418 come into contact with one another resulting in a decrease in the amount of unreacted scavenger material in the scavenger volume 418 and neutralization of the H2S in the sample.

After taking a sample of the fluid, the fluid sampling tool 170 may be returned to the surface and the sample chamber 305 prepared for removal from the fluid sampling tool 170 by shutting valve 414. In a wireline or slickline operation, this may be done immediately or almost immediately after the sample is taken. In a MWD or LWD operation, the return to the surface may not happen until some reason occurs to withdraw the entire drill string from the borehole. In each case, however, a control system onboard the fluid sampling tool 170, at the surface controller 184 or at another location may log location data corresponding to the location within the formation front which each sample was taken. For example, each sample chamber 305, 310, 315 may be filled with fluid from a different depth that corresponds to specific location data.

In an embodiment, the sample chamber 305 is agitated to move the scavenger volume 418 within the sample compartment 412, causing the scavenger volume 418 to mix and come into contact with the formation fluids and any unreacted H2S therein, furthering the reaction between the scavenger and the H2S. After a sufficient time, when all H2S has been reacted with the scavenger, the fluid sample may be analyzed to determine the concentration of H2S within the well fluid. In an embodiment, this analysis may include disassembling the sample chamber 305 and removing and analyzing the scavenger volume 418.

As noted above, the scavenger may be formed from a variety of materials, and may react with the H2S in any number of ways. The process for analyzing a sample may also vary significantly depending on the type of scavenger used, and whether the reaction between the scavenger in the H2S is a regenerative or non-regenerative reaction. As referenced herein, a regenerative reaction is a reaction with a contaminant that can be undone in a lab environment to determine the concentration of the contaminant by measuring it directly. In the case of H2S, regenerative scavengers may include sodium hydroxide (NaOH, or lye) and potassium hydroxide (KOH), and alkanolamines such as ethanolamine and diethanolamine. Such scavengers react with H2S to form compound bonds that can be displaced by, for example, heating or gas stripping. Upon displacement of the bonds, the concentration of the H2S may be accurately measured using any suitable method, such as gas chromatography or inductively coupled plasma atomic emission spectroscopy (ICP-AES).

Metal scavengers such as iron, zinc, copper, and silver that react with H2S to produce insoluble sulfides are also examples of regenerative scavengers. Using such scavengers, the solid can be recovered by filtration and measured by any number of techniques, including treatment to solubilize the metal, the concentration of which may be determined using ICP, using colourimetric methods, or electrochemically. Similarly, strong acid can be used to regenerate the H2S, which is measured using an appropriate technique. Organic scavengers can also be used, and the concentration of either the reagent or byproduct of the reaction between the reagent and H2S can be measured to determine the concentration of H2S in the fluid sample.

By using a regenerative scavenger to react the H2S with the scavenger during sampling and regenerating the H2S with a secondary reaction prior to analysis, H2S concentrations may be directly measured in a lab environment while ensuring that the volatile H2S gas is not reacted during transport from the sample site. This may be especially useful in cases where only a small amount of H2S is present, for example less than 20 ppm or between 20 and 50 ppm, and the H2S may not be otherwise detectable.

In another embodiment, a non-regenerative scavenger may be applied as a trap or converter material prior to analysis of the fluid sample. Examples of non-regenerative scavengers include bases such as lye, certain implementations of metal scavengers such as silver, and other oxidizers. Such other oxidizers may include potassium permanganate (KMnO4), and potassium dichromate (K2Cr2O7). These types of reagents oxidize sulfide to sulfate, a byproduct which may subsequently be analyzed to determine the concentration of H2S in the fluid sample as it was taken from the formation. Other oxidizers, such as peroxide, persulphate, percarbonate, cerium salts, chorate, or bromate may be used as scavengers in a similar manner.

In another embodiment, ferric ions (Fe+3) may be used as scavengers that react with the H2S to form ferrous iron (Fe+2), elemental sulphide, and hydrogen gas. In such an embodiment, the fluid sample may be assayed to determine the concentration of ferrous iron, which in turn would indicate the initial concentration of H2S.

Applying similar methods, triazines may be reacted with the H2S to form dithiane and trithiane, and polyamines may be catalyzed by quat salts. Other scavenger materials may include reactive aldehydes such as acrolein, gluteraldehyde, and glyceraldehyde, silver or ferrous metal charged ion exchange resins, amine or sodium form ion exchange resins, and other solid adsorbents such as proprietary macroreticular resins, including Amberlite XAD-2, Carbotrap, Carbopak, or Carbosieve available from Sigma Aldrich.

In an embodiment, the sample compartment includes a sufficient amount of scavenger to react with a maximum estimated amount of H2S that may be included within the sample fluid. For example, the scavenger may be NaOH, which has a mole weight of 40 g/mole. H2S has a mole weight of 34.08 g/mole, and in this example, the NaOH and H2S are reacted to form Na2S and H2O. It follows that at least approximately 2.34 (or 2(40/34.08)) grams of NaOH per gram of H2S is needed to react with the H2S. Thus, if it is estimated that a sample compartment may contain at most 1.0 grams of H2S, an operator may select a scavenger volume of at least 2.34 grams to ensure that all H2S in the sample compartment is reacted.

In an embodiment in which the scavenger forms a solid object, such as a sphere, an analyst may measure the size of the sphere after reaction with the fluid sample and compare the reacted size to the initial size of the sphere. In such an embodiment, the change in size of the scavenger volume may provide an indication as to the concentration of H2S in the fluid. In another embodiment, the scavenger may be formed from multiple small objects, such as pellets, grains, or a solution containing such pellets or grains or other compositions of scavenger material, and the concentration of H2S in the fluid sample may be determined by distilling and measuring the remaining amount of scavenger material.

According to an illustrative embodiment, a method for determining the concentration of H2S in a wellbore fluid includes measuring the concentration of a byproduct created when the scavenger reacts with $H_2S$ in the fluid sample in the sample compartment, and determining a concentration of H2S in the wellbore fluid based on the measured concentration of byproduct. In another embodiment, the method includes measuring the concentration of scavenger material that did not react with H2S and determining a concentration of H2S in the wellbore fluid based on the measured concentration of remaining scavenger material. In yet another embodiment, the method includes breaking a bond between the H2S and the scavenger and directly measuring the concentration of H2S after freeing the H2S from the scavenger.

The illustrative systems, methods, and devices described herein may also be described by the following examples:

Example 1. A downhole sample chamber for sampling fluid from a formation, the chamber having:
  a fluid inlet;
  a fluid outlet;
  a compartment between the fluid inlet to fluid outlet; and
  a scavenger volume within the compartment, wherein the scavenger volume is reactive with H2S.

Example 2. The downhole sample chamber of example 1, wherein the compartment comprises a sample fluid containing H2S, and wherein the scavenger volume comprises an amount of scavenger composition that is selected to react with a maximum estimated amount of H2S included within the sample fluid.

Example 3. The downhole sample chamber of examples 1 or 2, wherein the scavenger volume comprises a spherical volume.

Example 4. The downhole sample chamber of example 3, wherein a change in size of the spherical volume is indicative of an amount of H2S in the sample fluid.

Example 5. The downhole sample chamber of examples 1-4, wherein the scavenger volume is reactive with H2S in a non-regenerative reaction.

Example 6. The downhole sample chamber of examples 1-4, wherein the scavenger volume is reactive with H2S in a regenerative reaction.

Example 7. The downhole sample chamber of examples 1-4, wherein the scavenger volume comprises a composition selected from the group consisting of iron, zinc, copper, silver, ferrous gluconate, zinc salt, silver salt, formaldehyde, acrolein, glyoxal, and amines.

Example 8. A method for analyzing a sample from a wellbore, the method comprising:

inserting a sample chamber into a wellbore, the sample chamber having a fluid inlet, a fluid outlet, a compartment between the fluid inlet and fluid outlet, and a scavenger within the chamber, wherein the scavenger is reactive with $H_2S$;

circulating a wellbore fluid through the chamber to capture a sample of the wellbore fluid;

retrieving the sample chamber from the wellbore; and analyzing the sample to determine the concentration of $H_2S$ in the wellbore fluid.

Example 9. The method of example 8, wherein analyzing the sample to determine the concentration of $H_2S$ in the wellbore fluid comprises measuring a concentration of a byproduct created when the scavenger reacts with $H_2S$ and determining a concentration of $H_2S$ in the wellbore fluid based on the measured concentration of byproduct.

Example 10. The method of example 8, wherein analyzing the sample to determine the concentration of $H_2S$ in the wellbore fluid comprises measuring a concentration of scavenger material that did not react with $H_2S$ and determining a concentration of $H_2S$ in the wellbore fluid based on the measured concentration of remaining scavenger material.

Example 11. The method of example 8, wherein analyzing the sample to determine the concentration of $H_2S$ in the wellbore fluid comprises breaking a bond between the H2S and the scavenger.

Example 12. The method of example 11, wherein analyzing the sample to determine the concentration of $H_2S$ in the wellbore fluid further comprises directly measuring the concentration of $H_2S$ after breaking the bond between the scavenger and H2S.

Example 13. The method of examples 8-12, wherein the scavenger comprises an amount of scavenger composition that is selected to react with a maximum estimated amount of H2S included within the sample.

Example 14. The method of examples 8-12, wherein the scavenger comprises a sphere, and wherein analyzing the sample to determine the concentration of H2S in the wellbore fluid comprises measuring a change in diameter of the sphere.

Example 15. A system for sampling fluid from a formation, the system having:

a probe to extend and engage a portion of the formation exposed in a wellbore;

a pump coupled to the probe for pumping fluid from the formation; and a sample compartment coupled to the pump to receive at least a sample portion of the fluid pumped from the formation through the probe;

wherein the sample compartment includes a scavenger volume.

Example 16. The system of example 15, wherein the scavenger volume comprises an amount of scavenger composition that is selected to react with a maximum estimated amount of H2S to be measured within the sample fluid.

Example 17. The system of examples 15 or 16, wherein the scavenger volume comprises a spherical volume.

Example 18. The system of examples wherein the scavenger volume is reactive with H2S to form a regenerative byproduct that is indicative of a concentration of H2S in the fluid.

Example 19. The system of examples 15-17, wherein the scavenger volume is reactive with H2S to form a non-regenerative byproduct that is indicative of a concentration of H2S in the fluid.

Example 20. The system of example 19, wherein the scavenger volume comprises lye.

It should be apparent from the foregoing that an invention having significant advantages has been provided. While the invention is shown in only a few of its forms, it is not limited to only these embodiments but is susceptible to various changes and modifications without departing from the spirit thereof

We claim:

1. A system for sampling fluid from a formation, the system comprising:

at least one probe to extend from a fluid sampling tool and engage a portion of the formation exposed in a wellbore;

a pump coupled to the probe for pumping fluid from the formation; and a sample compartment comprising:

a fluid inlet coupled to the pump to receive at least a sample portion of the fluid pumped from the formation through the probe;

a fluid outlet;

a compartment between the fluid inlet and the fluid outlet, the compartment comprising a pressurized side and a sample side separated by a sample piston;

and a volume of scavenger material within the sample side of the compartment, wherein retraction of the sample piston allows the volume of scavenger material to contact any hydrogen sulfide present in the sample fluid in the sample side.

2. The system of claim 1, wherein the volume of scavenger material comprises an amount of scavenger composition that is selected to react with a maximum estimated amount of hydrogen sulfide to be measured within the sample fluid.

3. The system of claim 1, wherein the scavenger volume comprises a spherical volume.

4. The system of claim 1, wherein the volume of scavenger material is reactive with hydrogen sulfide to form a regenerative byproduct that is indicative of a concentration of hydrogen sulfide in the fluid.

5. The system of claim 1, wherein the volume of scavenger material is reactive with hydrogen sulfide to form a non-regenerative byproduct that is indicative of a concentration of hydrogen sulfide in the fluid.

6. The system of claim 5, wherein the volume of scavenger material comprises lye.

7. The system of claim 1, further comprising a hydrogen sulfide detection device.

8. The system of claim 7, wherein the hydrogen sulfide detection device measures an unreacted volume of scavenger material.

9. The system of claim 7, wherein the hydrogen sulfide detection device comprises at least one of a chromatograph, a spectrometer, a colorimeter, an assay device, or an electrochemical device.

10. The system of claim 7, wherein the hydrogen sulfide detection device is located outside the wellbore.

11. The system of claim 7, wherein the hydrogen sulfide detection device is within the wellbore.

12. The system of claim 7, wherein the hydrogen sulfide detection device is configured to break a bond between the hydrogen sulfide and the scavenger volume.

13. The system of claim 12, wherein the hydrogen sulfide detection device is further configured to measure a concentration of hydrogen sulfide after breaking the bond.

14. The system of claim 7, wherein the sample compartment comprises an inlet and an outlet, and at least one of the inlet or the outlet is fluidly coupled to the hydrogen sulfide detection device.

15. The system of claim 1, wherein the scavenger volume is contained within a volume tethered to the sample compartment.

16. The system of claim 1, wherein the sample compartment is configured to release the scavenger volume after the sample compartment is closed.

* * * * *